(12) United States Patent
Kim et al.

(10) Patent No.: US 8,525,130 B2
(45) Date of Patent: Sep. 3, 2013

(54) METHOD FOR MEASURING BIOLOGICAL CONTAMINATION OF SEA WATER DESALINATION FACILITY AND SYSTEM THEREOF

(75) Inventors: Joon-Ha Kim, Buk-gu (KR); Kyung Hwa Cho, Buk-gu (KR); In Seop Chang, Buk-gu (KR); Hyunjung Kim, Buk-gu (KR); Jinhee Choi, Buk-gu (KR)

(73) Assignee: Gwangju Institute of Science and Technology, Buk-gu, Gwangju (KR)

( * ) Notice: Subject to any disclaimer, the term of this patent is extended or adjusted under 35 U.S.C. 154(b) by 42 days.

(21) Appl. No.: 13/301,148

(22) Filed: Nov. 21, 2011

(65) Prior Publication Data

US 2013/0126754 A1    May 23, 2013

(51) Int. Cl.
   *G01N 21/64*   (2006.01)
(52) U.S. Cl.
   USPC ........................................... 250/459.1

(58) Field of Classification Search
   USPC ............................................ 250/459.1, 458.1
   See application file for complete search history.

(56) References Cited

U.S. PATENT DOCUMENTS 5,700,370 A * 12/1997 Helmo ............................ 210/94
2003/0039700 A1 * 2/2003 Sasaki et al. .................. 424/547

* cited by examiner

*Primary Examiner* — Kiho Kim
(74) *Attorney, Agent, or Firm* — Nath, Goldberg & Meyer; Joshua B. Goldberg; Lakshmi Rajan

(57) ABSTRACT

The present invention relates to a method for measuring degree of biological contamination in a sea water desalination facility, and is characterized by comprising the following steps of: a) collecting any one selected from a group consisting of raw sea water flowing into the sea water desalination facility, pre-treated water prepared by pre-treating the raw sea water, product water (permeate) produced after the pre-treated water goes through a desalination process and brine; and b) measuring wavelength and strength of a natural phosphor, which is contained in the raw sea water, pre-treated water, product water (permeate) or brine, using a fluorescence spectrophotometer.

6 Claims, 1 Drawing Sheet

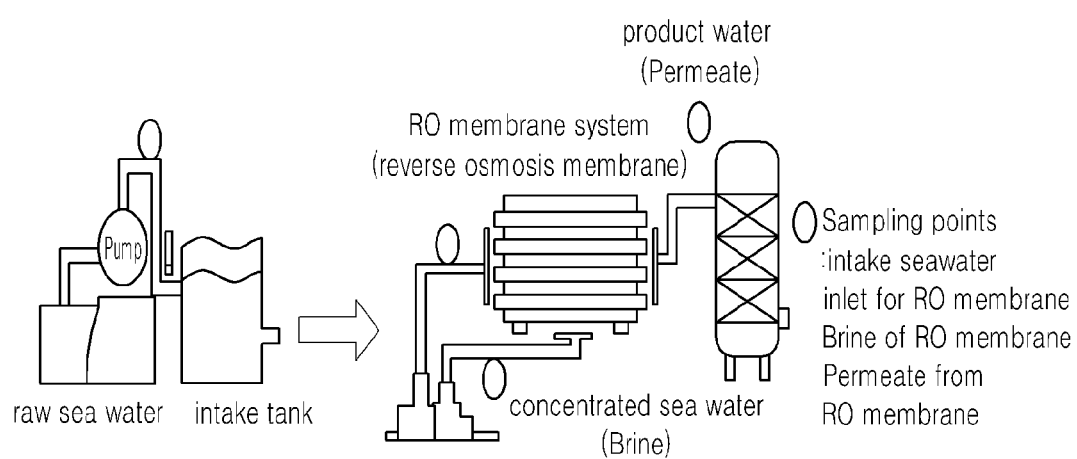

METHOD FOR MEASURING BIOLOGICAL CONTAMINATION OF SEA WATER DESALINATION FACILITY AND SYSTEM THEREOF

TECHNICAL FIELD

The present disclosure relates to a method for measuring biological contamination in a sea water desalination facility, and specifically, it relates to a method for measuring biological contamination of the sea water desalination facility, which can distinguish degree of biological contamination of a reverse osmosis membrane and its contamination source without further separation of desalination equipments such as the reverse osmosis membrane, and a system thereof.

BACKGROUND

In a sea water desalination facility, a membrane filtration process using a reverse osmosis membrane is broadly being applied to many industries or water treatment area as well as desalination of sea water, and its predominance has been proved in many ways such as performance or energy efficiency. On the other hand, in operating a reverse osmosis membrane filtration process, proliferation of microorganisms to the form of biofilm on the membrane surface of the treated water side (non-treated water side of the reverse osmosis membrane) causing increase of operating pressure of the reverse osmosis membrane, or biofouling (contamination caused by organism attachment) causing decrease of water permeability or separation performance of the reverse osmosis membrane become problems. The biofouling is a membrane surface fouling caused by various contaminants such as organic or inorganic floating particles, dissolved organic matters (DOM), dissolved solids and biogenic materials, and major contamination source is organic contamination related to large amount of organic matters.

"Biofilm" is a structure formed by microorganism on the pipe wall or the reverse osmosis membrane face when water flows therein, and mainly contains extra cellular polymeric substances consisting of polysaccharides, proteins and the like, and bacteria.

As countermeasures to the biofouling in the reverse osmosis membrane filtration plant, many techniques of adding a disinfectant which inhibits increase of the biofilm to treated water, and of adding a cleanser which cleans the reverse osmosis membrane were suggested. But, the method for accurately and easily evaluating or verifying effectiveness of condition for adding the disinfectant or cleanser by measuring degree of biofouling became a problem.

As the conventional methods for detecting biofouling, the first method is to analyze the structure of the biofilm itself without disassembling the reverse osmosis membrane or the biofilm, and uses atomic force microscope, optical coherence tomography, scanning electron microscope, magnetic resonance imaging, confocal laser scanning microscope and transmission electron microscope. But, there are problems that expensive devices and experts are needed, and only the biofouled surface can be checked.

The second method is a biological analysis method such as real-time monitoring of amplified product of PCR (real-time PCR), restriction fragment length polymorphism (RFLP) analysis, denaturing gradient gel electrophoresis (DGGE) gene analysis, fluorescence in situ hybridization and the like, but it has problems of taking several days and requiring experts.

The third method is to quantitatively analyze biofouling by biomass accumulation, and may include ATP measuring method, total direct cell count (TDC), heterotrophic plate count (HPC) and the like, but theses technologies has problems that it also needs expert knowledge, and consumes chemical enzyme. And TDC has a problem of large standard deviation, and HPC has a problem that only small part of the microorganism sample can be checked.

Therefore, a method which can quickly monitor degree of biofouling (biological contamination) without separation or disassembly of equipments such as a reverse osmosis membrane in a sea water desalination facility is needed, and further, there has been no biofouling monitoring method using a natural phosphor contained in brine in the sea water desalination facility.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

Accordingly, an object of the present invention is to provide a method for measuring biological contamination of a sea water desalination facility without further separation of equipments in the sea water desalination facility.

Another object of the present invention is to provide a system for measuring biological contamination of a sea water desalination facility using a fluorescence spectrophotometer in the sea water desalination facility.

In one aspect of the present invention, provided is a method for measuring biological contamination of a sea water desalination facility comprising the following steps of:
  a) collecting any one selected from a group consisting of raw sea water flowing into the sea water desalination facility, pre-treated water prepared by pre-treating the raw sea water, product water (permeate) produced after the pre-treated water goes through a desalination process and brine; and
  b) measuring wavelength and strength of a natural phosphor, which is contained in the raw sea water, pre-treated water, product water (permeate) or brine, using a fluorescence spectrophotometer.

According to one embodiment of the present invention, wavelength range of the fluorescence spectrophotometer may be 220~600 nm.

According to one embodiment of the present invention, the natural phosphor is at least one selected from a group consisting of lipo-pigment, nicotinamide adenine dinucleotide phosphate (NADPH), nicotinamide adenine dinucleotide (NADH), flavin coenzyme, tyrosine, tryptophan, fulvic acid and humic acid.

According to one embodiment of the present invention, the sea water desalination facility may be a reverse osmosis membrane filtration plant comprising a raw water intake part, a pre-treatment part and a reverse osmosis filter containing an osmosis membrane module.

In another aspect of the present invention, provided is a system for measuring biological contamination of a sea water desalination facility, wherein the sea water desalination facility further comprises a fluorescence spectrophotometer detecting a natural phosphor from any one selected from a group consisting of raw sea water flowing into the sea water desalination facility, pre-treated water prepared by pre-treating the raw sea water, product water (permeate) produced after the pre-treated water goes through a desalination process and brine.

According to one embodiment of the present invention, the sea water desalination facility may be a reverse osmosis membrane filtration plant comprising a raw water intake part, a pre-treatment part and a reverse osmosis filter containing an osmosis membrane module.

BRIEF DESCRIPTION OF THE DRAWINGS

FIG. 1 is a diagram of a sea water desalination plant containing a reverse osmosis system. Circles are sampling points of raw sea water before pre-treatment, pre-treated water after pre-treatment but before passing through a RO membrane, brine and product water (permeate), respectively.

DETAILED DESCRIPTION

Hereinafter, the present invention is described in detail.

The present invention is to measure degree of biofouling (biological contamination caused by organism attachment) of equipments in a sea water desalination facility, the equipments may be an intake pump, an intake pipe, pipes of a desalination process, a filter membrane and the like. Particularly, according to the preferred embodiment of the present invention, the present invention is characterized that in a sea water desalination plant using a reverse osmosis membrane system, replacement period of a reverse osmosis membrane system, or the injection amount of a disinfectant and cleanser can be decided in advance by detecting degree of biofouling (biological contamination caused by organism attachment) of the reverse osmosis membrane and its contamination source.

As shown in FIG. 1, the present invention relates to a method for measuring degree of biofouling of the reverse osmosis (RO) membrane filter and its contamination source in the sea water desalination plant system using the RO membrane system by collecting raw sea water, pre-treated water which passed through an intake tank and then pre-treated, product water (permeate) which passed through a filter membrane system and brine; and detecting each natural phosphors contained in the collected samples using a fluorescence spectrophotometer without further separation of the filter membrane from the plant.

Accordingly, the present invention measures degree of biological contamination of a sea water desalination facility and its contamination source by collecting raw sea water, pre-treated water, product water (permeate) or brine, respectively, and measuring wavelength and strength of a natural phosphor, which is contained in the raw sea water, pre-treated water, product water (permeate) or brine, using a fluorescence spectrophotometer.

The raw sea water may be directly collected from the surface layer of ocean or deep water, and the pre-treated water refers to water prepared by subjecting the raw sea water to membrane treatment using a sand filter, a microbble, ultrafiltration membrane or microfiltration membrane, a loose reverse osmosis membrane and the like. The product water refers to permeate prepared by passing the pre-treated water through a filter containing a reverse osmosis module, and the brine refers to non-permeate to be discarded to ocean.

According to one preferred embodiment of the present invention, the fluorescence spectrophotometer is a Three-dimensional excitation-emission (EEM) fluorescence spectroscopy, and it is preferred to have high sensitivity and selectivity without sample degradation. Accordingly, the fluorescence spectrophotometer is characterized by short sample analysis time figuring out the characteristic of a dissolved organic matter (DOM) and easy handling.

According to the preferred embodiment of the present invention, the natural phosphor may be lipo-pigment, nicotinamide adenine dinucleotide phosphate (NADPH), nicotinamide adenine dinucleotide (NADH), flavin coenzyme, tyrosine, tryptophan, fulvic acid or humic acid.

According to the preferred embodiment of the present invention, wavelength range of the fluorescence spectrophotometer according to the present invention may be 220~600 nm.

The biofouling is membrane surface fouling caused by various contaminants The contaminants may include organic or inorganic floating particles, dissolved organic matters (DOM), dissolved solids and biogenic materials, and may be major contamination source in the most sea water desalination process.

Bacterial cell surface comprises lipopolysaccharides (LPS), which is a kind of dissolved organic matter interacting with the cell surface, and extra cellular polymeric substances (EPS) of membrane, and the bacterial cell comprises natural phosphors such as amino acids, lipo-pigments, nicotinamide adenine dinucleotide phosphate (pyridinic NADPH), flavin coenzymes and the like. Kinds of the phosphors can be confirmed by detecting the natural phosphors because they have characteristic excitation and emission (fluorescence) wavelength.

In the early stage of biofouling, most materials form a biofilm by being attached to the sea water desalination facility, particularly the surface of the reverse osmosis membrane. After forming the biofilm, the process of falling off and re-attaching microorganism molecular aggregates is repeated. The materials float from the reverse osmosis membrane process to concentrated waste water, and at this time, biological contaminants such as lipopolysaccharides (LPS), extra cellular polymeric substances (EPS), dissolved organic matters (DOM) and nicotinamide adenine dinucleotides (NADH) are concentrated in brine. Because most of the biological contaminants are natural phosphors, biological contamination of the reverse osmosis membrane can be confirmed by detecting the natural phosphors in the brine.

Further, according to the preferred embodiment of the present invention, it is characterized that the present invention is a system for measuring biological contamination, wherein the reverse osmosis membrane filtration plant comprising a raw water intake part, a pre-treatment part and a reverse osmosis filter containing an osmosis membrane module further comprises a fluorescence spectrophotometer detecting a natural phosphor from each of raw sea water of the raw water intake part, pre-treated water which passed through the pre-treatment part, and brine and product water (permeate) which passed through the reverse osmosis membrane filter.

The system of the present invention may be a system for measuring biological contamination of the reverse osmosis membrane, which can detect the natural phosphor contained in the brine by further comprising the three-dimensional excitation-emission (EEM) fluorescence spectroscopy according to the preferred embodiment of the present invention to the intake tank intaking the raw sea water and the pipe where the brine, which passed through the RO membrane system, flows of the general reverse osmosis membrane filtration plant of FIG. 1.

In the sea water desalination facility according to the present invention, the collecting of the sample to measure biological contamination is described with the raw sea water, the pre-treated water, the product water (permeate) and brine (non-permeate), but it is obvious to a person skilled in the art that the sample can be collected from various equipments in the sea water desalination facility, for example, an intake pipe, an intake tank, a pre-filtration device, various pumps and pipes, a filter such as a reverse osmosis membrane module, a discharge pipe and the like, respectively to measure the degree of biological contamination.

EXAMPLE

Hereinafter, the present invention will be more particularly described by the preferred examples. However, these are intended to illustrate the invention as preferred embodiments of the present invention and do not limit the scope of the present invention.

Example 1

Firstly, the brine samples were collected from reverse osmosis membrane plants located at Fujairah (United Arb Emirates), Yeon-do (South Korea), Tok-do (South Korea), respectively. The samples were collected from four points of the plants located at Yeon-do and Tok-do, respectively, and the four points are raw sea water, pre-treated water right before entering the RO membrane system, brine and product water which passed through the RO membrane, respectively. Further, feed water and biologically contaminated membrane of the Fujairah plant were used.

The samples were analyzed with a spectrophotometer (F-2500 FL spectrophotometer, Hitachi High-Technologies Corporation, Japan), and the excitation and emission were conducted at the range of 220~600 nm with sampling interval of 10 nm. The excitation and emission slits were maintained to 5 nm, and the scanning speed was set to 3000 nm/min to analyze the samples.

As a result, it was confirmed that there were many proteins and various dissolved organic matters in the raw sea water and the brine.

The peak pattern of the brine was simpler than that of the raw sea water, and it means that most biological contamination sources are made up of biologically similar synthetic molecules. Therefore, the biological contamination sources can be separated by the fluorescence spectrophotometer.

Fluorescent excitation and emission wavelength and strength data to the samples collected from the sea water desalination plant at Yeon-do and Tok-do were listed in Tables 1 and 2, respectively.

In the following tables, DOC refers to dissolved organic carbon, and, Cond refers to conductivity.

TABLE 1

| Yeon-do | DOC (mg/L) | Cond. (mS/cm) | peak 1 (220/290) strength | peak 2 (270-280/ 410-440) strength | peak 3 (330/410) strength | peak 4 (230/ 330-340) strength |
|---|---|---|---|---|---|---|
| Raw sea water | 3.83 | 34.1 | 79.91 | 132.7 | 96.18 | 60.70 |
| Brine | 3.99 | 42.0 | 76.39 | 80.80 | 91.97 | 38.52 |
| Pre-treated water | 4.22 | 36.4 | 83.44 | 72.07 | 84.51 | 63.96 |
| Product water | 0.54 | 0.39 | 149.7 | — | — | 79.83 |

TABLE 2

| Tok-do | DOC (mg/L) | Cond. (mS/cm) | peak 1 (220/290) strength | peak 2 (250-260/ 400-410) strength | peak 3 (330-340/410) strength |
|---|---|---|---|---|---|
| Raw sea water | 7.37 | 50.8 | 115.3 | 76.72 | 118.1 |
| Brine | 7.09 | 51.1 | 125.8 | 52.59 | 84.17 |
| Pre-treated water | 7.35 | 50.6 | 109 | 92.74 | 89.99 |
| Product water | 0.49 | 0.58 | 142.6 | — | — |

As shown in Tables 1 and 2, the peak 1 and 4 are related to protein materials, the 2-1 is related to humic material, and the peak 3 is related to fulvic acid. It was confirmed that the peak strength in the wavelength range related to each material was more reduced in the brine than in the raw sea water. This meant that the reverse osmosis membrane was biofouled as much as the strength difference, and the degree of contamination and contamination source of each peak could be find out.

According to the present invention, the degree of biological contamination can be quickly measured by detecting natural phosphors contained in raw sea water, pre-treated water, product water (permeate) or brine without further separation or disassembly of equipments of a sea water desalination facility, and contamination sources can be distinguished. Therefore, replacement period of various equipments of a desalination process such as a reverse osmosis membrane, and the kind and amount of a disinfectant and cleanser put into the equipments can be decided.

While certain embodiments have been described, these embodiments have been presented by way of example only, and are not intended to limit the scope of the disclosures. Indeed, the novel methods and apparatuses described herein may be embodied in a variety of other forms; furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A method for measuring biological contamination of a sea water desalination facility comprising the following steps of:
   a) collecting any one selected from a group consisting of raw sea water flowing into the sea water desalination facility, pre-treated water prepared by pre-treating the raw sea water, product water (permeate) produced after the pre-treated water goes through a desalination process and brine; and
   b) measuring wavelength and strength of a natural phosphor, which is contained in the raw sea water, pre-treated water, product water (permeate) or brine, using a fluorescence spectrophotometer.

2. The method for measuring biological contamination of a sea water desalination facility of claim 1, wherein wavelength range of the fluorescence spectrophotometer is 220~600 nm.

3. The method for measuring biological contamination of a sea water desalination facility of claim 1, the natural phosphor is at least one selected from a group consisting of lipopigment, nicotinamide adenine dinucleotide phosphate (NADPH), nicotinamide adenine dinucleotide (NADH), flavin coenzyme, tyrosine, tryptophan, fulvic acid and humic acid.

4. The method for measuring biological contamination of a sea water desalination facility of claim 1, wherein the sea water desalination facility is a reverse osmosis membrane filtration plant comprising a raw water intake part, a pre-treatment part and a reverse osmosis filter containing an osmosis membrane module.

5. A system for measuring biological contamination of a sea water desalination facility, wherein the sea water desalination facility comprises a fluorescence spectrophotometer for measuring wavelength and strength of a natural phosphor from any one selected from a group consisting of raw sea water flowing into the sea water desalination facility, pre-treated water prepared by pre-treating the raw sea water, product water (permeate) produced after the pre-treated water goes through a desalination process and brine.

6. The system for measuring biological contamination of a sea water desalination facility of claim 5, wherein the sea water desalination facility is a reverse osmosis membrane filtration plant comprising a reverse osmosis filter, which contains a raw water intake part, a pre-treatment part and an osmosis membrane module.

* * * * *